US006852715B1

(12) United States Patent
Garcia Gravalos et al.

(10) Patent No.: US 6,852,715 B1
(45) Date of Patent: Feb. 8, 2005

(54) INDOLOCARBAZOLE ALKALOIDS FROM A MARINE ACTINOMYCETE

(75) Inventors: Dolores Garcia Gravalos, Madrid (ES); Julia Perez, Leon (ES); Librada Maria Cañedo, Leon (ES); Francisco Romero, Leon (ES); Fernando Espliego, Leon (ES)

(73) Assignee: Instituto Biomar S.A. (ES)

( * ) Notice: Subject to any disclaimer, the term of this patent is extended or adjusted under 35 U.S.C. 154(b) by 70 days.

(21) Appl. No.: 10/019,388

(22) PCT Filed: Jun. 28, 2000

(86) PCT No.: PCT/GB00/02473

§ 371 (c)(1),
(2), (4) Date: Apr. 23, 2002

(87) PCT Pub. No.: WO01/00627

PCT Pub. Date: Jan. 4, 2001

(30) Foreign Application Priority Data

Jun. 28, 1909 (GB) ............................................. 9915069

(51) Int. Cl.$^7$ .................... C07D 498/22; A61K 31/353; A61P 35/00
(52) U.S. Cl. .................................. 514/211.08; 540/546
(58) Field of Search ...................... 514/211.08; 540/546

(56) References Cited

FOREIGN PATENT DOCUMENTS

| JP | 05-247055 A | 9/1993 |
|---|---|---|
| WO | WO 94/04541 A | 3/1994 |

OTHER PUBLICATIONS

Draetta, G. and Pagano, M. in "Annual Reports in Medicinal Chemistry, vol. 31", 1996, Academic Press, San Diego, p 241–246.*

Bergeron et al., "Antineoplastic and Antiherpetic Activity of Spermidine Catecholamide Iron chelators", *Biochem. Biophys. Res. Comm.*, vol. 121, No. 3, pp. 848–854 (1984).

Hasegawa et al., "A Rapid Analysis for Chemical Grouping of Aerobic Actinomycetes", *The Journal of General and Applied Microbiology*, vol. 29, pp. 319–322 (1983).

Nishizuka, Y., "The molecular heterogeneity of protein kinase C and its implications for cellular regulation", *Nature*, vol. 334, pp. 661–665 (1988).

Nishizuka, Y., "The role of protein kinase C in cell surface signal transduction and tumour promotion", *Nature*, vol. vol. 308, pp. 693–698 (1984).

Schroeder et al., "Synthesis and Biological Effects of Acyclic Pyrimidine Nucleoside Analogues", *J. Med. Chem.*, vol. 24, pp. 1078–1083 (1981).

Shirling et al., "Methods for Characterization of Streptomyces Species", *Int. J. Syst. Bacteriol.*, vol. 16, No. 3, pp. 313–340 (1966).

Van der Auwera et al., "Identification of Bacteriodes by cellular fatty acid profiles: application to the routine microbiological laboratory", *J. Microbiol. Methods*, vol. 4, No. 5/6, pp. 267–275 (1986).

* cited by examiner

Primary Examiner—Thomas C. McKenzie
(74) Attorney, Agent, or Firm—Fish & Richardson, P.C.

(57) ABSTRACT

The invention provides compounds of formula (1) wherein $R^1$ is a hydrogen atom, an alkyl group having 1 to 6 carbon atoms or an alkoxy group having 1 to 6 carbon atoms; and $R^2$ is a hydrogen atom, an alkyl group having 1 to 6 carbon atoms or an alkoxy group having 1 to 6 carbon atoms; and pharmaceutically acceptable salts thereof. The invention also relates to a process for obtaining the compounds, compositions containing them and their therapeutic use. The compounds display excellent activity against mammalian cancer cell lines.

14 Claims, No Drawings

INDOLOCARBAZOLE ALKALOIDS FROM A MARINE ACTINOMYCETE

FIELD OF THE INVENTION

New indolocarbazole alkaloids have been isolated from the culture broth of a staurosporine-producing actinomycete (CLCO-002). Their production by aerobic fermentation under controlled conditions of the strain, and the isolation and purification of compounds are described herein. The compounds and the fermentation broth demonstrate significant activity against several cancer cell lines.

BACKGROUND OF THE INVENTION

The isoenzyme family of protein kinase C (PKC) plays a key role in signal transduction and cellular regulation (Y. Nishizuka, 1988). From the observation that the tumor promoting phorbol esters are able to stimulate PKC activity (Y. Nishizuka, 1984), it was concluded that inhibitors of this enzyme could be useful for cancer chemotherapy. PKC inhibitors have been extensively investigated as potential drugs for the treatment of cancer. Accordingly, a goal of the present invention is to provide new antitumor agents; these compounds are alkaloids with significant activity against several cancer cell lines.

Yet another objective of this invention is to provide pharmaceutical compositions for administering to a patient in need of treatment using the active compounds described herein.

Microbial products are interesting because their industrial production is well established at present times. Therefore, another objective of this invention is directed to the production of the active compounds and to their isolation and purification from the resulting fermentation broth.

SUMMARY OF THE INVENTION

This invention provides compounds of formula (1).

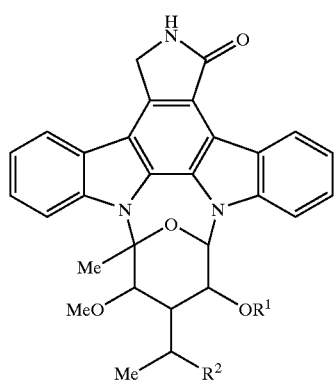

(1)

wherein:
$R^1$ is a hydrogen atom, an alkyl group having 1 to 6 carbon atoms or an alkoxy group having 1 to 6 carbon atoms; and
$R^2$ is a hydrogen atom, an alkyl group having 1 to 6 carbon atoms or an alkoxy group having 1 to 6 carbon atoms;
and pharmaceutically acceptable salts thereof.

In the definitions of the groups $R^1$ and $R^2$ in formula (1), the alkyl groups and the alkyl moiety of the alkoxy groups are a straight or branched chain alkyl group having 1 to 6 carbon atoms such as methyl, ethyl, propyl, isopropyl, butyl, isobutyl, sec-butyl, tert-butyl, pentyl, neopentyl and hexyl.

It is preferred that $R^1$ and $R^2$ independently represent a hydrogen atom or an alkyl group having from 1 to 4 carbon atoms, particularly a hydrogen atom, a methyl group or an ethyl group.

In a particularly preferred embodiment, the present invention relates to 4'N-methyl-5'-hydroxystaurosporine (IB-97224) and 5'-hydroxystaurosporine (IB-97225), with structural formulae:

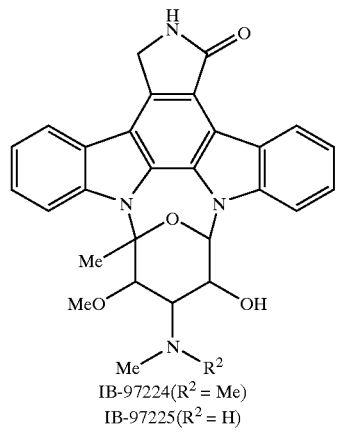

IB-97224($R^2$ = Me)
IB-97225($R^2$ = H)

In this invention the process of obtaining compounds of formula (1) or a pharmaceutically acceptable salt thereof is also described. The process comprises cultivating a strain of a microorganism capable of producing a compound of formula (1), recovering the compound of formula (1) from the cultured broth, and, optionally, satisfying the recovered compound.

An especially preferred process for producing compounds IB-97224 and IB-97225 comprises cultivating a strain of a microorganism capable of producing IB-97224 and IB-97225 in an aqueous nutrient medium with assimilable carbon and nitrogen sources and salts, under controlled submerged aerobic conditions. The compounds IB-97224 and IB-97225 are recovered and purified from the cultured broth.

The preferred culture is strain CLCO-002, and its chemical, biochemical and morphological characters show that it belongs to the *Actimomicetales* group. Other actinomycete strains also be used in the process according to the invention.

As described above, the compounds of formula (1), especially IB-97224 and IB-97225, have been found to have good activity against murine and human tumor cell lines, including P-38$D_1$, HT-29, A-549 and SK-MEL-28.

Therefore, the invention also provides a method for the treatment or prophylaxis of malignant tumours in a mammal, comprising administering to a mammal in need of such treatment an effective amount of a compound of formula (1) as defined above or a pharmaceutically acceptable salt thereof.

The invention further relates to the use of a compound of formula (1), as defined above, or a pharmaceutically acceptable salt thereof in the manufacture of a medicament for the treatment or prophylaxis of malignant tumours in a mammal.

The present invention also relates to pharmaceutical preparations which contain as an active ingredient compounds of formula (1), or a pharmaceutically acceptable salt thereof, together with a pharmaceutically acceptable carrier or diluent as well as the processes for its preparation.

Examples of pharmaceutical compositions include any solid (tablets, pills, capsules, granules, etc.) or liquid (solutions, suspensions or emulsions) with suitable composition for oral, topical or parenteral administration, and they may contain the pure compounds or in combination with any carrier or other pharmacologically active compounds. These compositions may need to be sterile when administered parenterally.

The correct dosage of a pharmaceutical composition of will vary according to the particular formulation, the mode of application, and the particular situs, host and bacteria or tumor being treated. Others factors like age, body weight, sex, diet, time of administration, rate of excretion, condition of the host, drug combinations, reaction sensitivities and severity of the disease shall be taken in account. Administration can be carried out continuously or periodically within the maximum tolerated dose.

DETAILED DESCRIPTION OF THE INVENTION

The Producing Organism

The microorganism utilised for the production of these new compounds is preferably an actinomycete strain, particularly actinomycete strain CLCO-002, a culture of which has been deposited in the Coleccion Española de Cultivos Tipo at the University of Valencia, Spain under the accession number CECT-3347. This deposit has been made under the provisions of the Budapest Treaty and all restrictions on the availability thereof to the public will be irrevocably maintained upon the granting of a patent on this application.

The organism was isolated from an unidentified marine sponge collected in Canary Islands waters.

All cultures were incubated at 27° C. and records of results were made weekly up to 21 days.

A description of the organism is as follows:

Morphology

The culture media utilised for this study were, ISP media No 2, 4, 5 and 6 (Shirling and Gotlieb, 1966), ATCC medium No 172 (American Type Culture Collection Catalog, 1989), Czapek Agar (Atlas, 1993), Bennet Agar (Atlas, 1993), 1.5% Water Agar (Luedemann). All media were supplemented with 50% artificial seawater. After 21 days at 28° C. growth was studied. Several shades of orange were observed. No aerial mycelium was formed. Substrate mycelium was branched. No soluble pigment was observed.

Physiological Characteristics

For carbon and nitrogen utilization studies ISP-9 was used (Shirling & Gotlieb, 1966). Due to low growth rate of CLCO-002 under defined media, the carbon and nitrogen utilisation tests showed residual growth so no clear results could be obtained. NaCl resistance was determined by using ATTC's 172 medium containing increasing concentrations of NaCl. The optimal concentration of salt was 1%. No growth was observed with 7% salt.

Cell Chemical Composition

Aminoacids:
  Diaminopimelic acid was determined by the method of Hasegawa et al. (1983). The meso-2,6-Diaminopimelic acid isomer was present in the whole cell hydrolysate of strain CLCO-002.

Fatty acids:
  FAMEs were determined by the method of Van der Auwera et al. (1986). The FAME composition as well as comparison with other similar strains is described in Table 1.

While the deposited organism is clearly preferred, the present invention is not restricted or limited to this particular strain or organisms. It is the intention of the present inventors to include any other producing organisms, strains or mutants within the scope of this invention.

TABLE 1

FAME composition of strain CLCO-002 and other actinomycete strains.
Composition is given as percentage of total fatty acids content.

| | 13:0 | i-14:0 | 14:0 | i-15:0 | a-15:0 | 15:0 | i-16:1 | i-16:0 | 16:1 | 16:0 | i-17:1 | i-17:0 | a-17:0 |
|---|---|---|---|---|---|---|---|---|---|---|---|---|---|
| CLCO-002 | <1 | <1 | <1 | 16.91 | 3.94 | 6.71 | <1 | 31.83 | <1 | <1 | 3.73 | <1 | <1 |
| STALBUS | <1 | 6.52 | <1 | 9.88 | 22.92 | <1 | 5.50 | 25.29 | <1 | 3.75 | 1.28 | 3.38 | 8.60 |
| SPAMETH | 1.21 | 10.34 | <1 | 1.86 | <1 | 4.30 | <1 | 15.51 | 5.63 | 8.62 | 1.08 | <1 | <1 |
| SPVIRIDO | <1 | 4.04 | 1.10 | 18.94 | 2.71 | 4.89 | <1 | 26.44 | <1 | 4.43 | <1 | 2.60 | 1.58 |
| AMCITRE | <1 | <1 | 3.18 | <1 | <1 | 1.03 | <1 | 6.37 | 12.62 | 40 | <1 | <1 | <1 |
| APBRAZIL | <1 | 3.15 | <1 | 15.46 | 18.91 | 2.76 | <1 | 19.07 | 2.15 | 1.79 | <1 | 2.39 | 9.64 |
| AMPDIGIT | <1 | 11.57 | <1 | 11.21 | 9.96 | <1 | 2.87 | 34.23 | <1 | 1.08 | <1 | 1.28 | 5.08 |
| AMYORIE | <1 | 3.40 | 2.37 | 19.94 | 4.66 | 1.17 | <1 | 11.85 | 5.59 | 18.41 | <1 | 2.99 | 4.44 |
| MNCHALC | <1 | 1.68 | <1 | 8.91 | 2.29 | 1.53 | 1.15 | 38.23 | <1 | 1.88 | 1.49 | 2.32 | 2.25 |
| MNECHCA | <1 | 1.17 | <1 | 6.97 | 1.24 | 2.81 | <1 | 30.88 | <1 | 2.29 | 1.63 | 4.11 | 1.68 |
| MNFUSCA | <1 | <1 | <1 | 26.56 | 6.53 | <1 | <1 | 8.58 | <1 | <1 | 7.30 | 11.89 | 13.25 |
| SACCAER | <1 | 3.06 | 1.35 | 14.41 | 8.62 | 1.04 | 5.68 | 20.07 | 13.84 | 6.16 | 4.55 | 2.20 | 5.31 |
| NOAFRI | 1.51 | 5.43 | 3.35 | 4.62 | <1 | 7.46 | 3.09 | 22.18 | 2.69 | 5.15 | 2.35 | <1 | <1 |
| MTSALMO | <1 | 1.12 | 1.28 | 6.75 | <1 | 7.83 | 7.53 | 21.58 | 1.21 | 1.97 | 1.01 | <1 | 1.07 |
| MTRUBRA | <1 | 1.40 | 1.38 | 4.12 | <1 | 3.41 | 7.27 | 25.00 | 2.63 | 3.89 | 2.17 | 1.08 | <1 |
| MTROSEO | 2.03 | 3.65 | 5.14 | 3.86 | <1 | 9.03 | 3.02 | 12.31 | 3.46 | 6.95 | 1.17 | <1 | <1 |
| AMROSEO | <1 | 2.19 | 1.24 | 6.73 | 1.09 | 6.94 | 1.43 | 22.21 | 2.21 | 3.61 | 2.74 | 1.03 | <1 |
| MTFERRU | 1.03 | 1.91 | 1.19 | 1.94 | <1 | 6.43 | 4.12 | 21.50 | 2.32 | 2.34 | <1 | <1 | <1 |

| | 17:1 | 17:0 | i-18:1 | i-18:0 | cis-18:1 | 18:0 |
|---|---|---|---|---|---|---|
| CLCO-002 | 24.33 | 3.31 | <1 | <1 | 4.13 | <1 |
| STALBUS | <1 | <1 | <1 | 1.09 | <1 | <1 |
| SPAMETH | 24.02 | 9.43 | 7.11 | <1 | 4.60 | 1.04 |
| SPVIRIDO | 11.36 | 8.58 | 7.48 | <1 | <1 | 1.16 |
| AMCITRE | <1 | 1.16 | <1 | <1 | 14.25 | 2.82 |
| APBRAZIL | 11.18 | 2.82 | <1 | <1 | 3.38 | 1.06 |
| AMPDIGIT | 4.39 | 1.64 | <1 | 1.76 | 7.60 | 1.54 |
| AMYORIE | 3.09 | 2.73 | <1 | <1 | 6.21 | 3.04 |

TABLE 1-continued

FAME composition of strain CLCO-002 and other actinomycete strains.
Composition is given as percentage of total fatty acids content.

| | | | | | | |
|---|---|---|---|---|---|---|
| MNCHALC | 5.43 | 6.95 | 14.58 | 1.31 | 1.28 | 2.68 |
| MNECHCA | 12.15 | 4.90 | 7.23 | <1 | 10.05 | 1.69 |
| MNFUSCA | 2.90 | 3.37 | 3.59 | <1 | 2.33 | 1.94 |
| SACCAER | 2.02 | <1 | <1 | <1 | <1 | 1.43 |
| NOAFR1 | 8.15 | 4.75 | 17.03 | <1 | <1 | 1.23 |
| MTSALMO | 11.58 | 5.53 | 17.34 | <1 | <1 | <1 |
| MTRUBRA | 6.84 | 4.97 | 15.44 | 1.25 | <1 | 1.61 |
| MTROSEO | 13.51 | 4.46 | 18.67 | <1 | 1.77 | <1 |
| AMROSEO | 10.97 | 4.33 | 17.84 | <1 | <1 | <1 |
| MTFERRU | 23.51 | 5.71 | 12.15 | 1.27 | 1.43 | <1 |

CLCO-002 = strain CLCO-002;
AMCITRE = *Actinomadura citrea* DSM 43461;
AMPDIGIT = *Ampullariella digitata* ATCC 15349;
AMROSEO = *Actinomadura roseoviolacea* DSM 43144;
AMYORIE = *Amycolatopsis orientalis* DSM 40040;
APBRAZIL = *Actinoplanes braziliensis* ATCC 25844;
MNCHALC = *Micromonospora chalcea* ATCC 31395;
MNECHCA = *Micromonospora echinospora calichinensis* NRRL 15839;
MNFUSCA = *Micromonospora fusca* NRRL B-3298;
MTFERRU = *Microtetraspora ferruginea* DSM 43553;
MTROSEO = *Microtetraspora roseola* ATCC 33579;
MTRUBRA = *Microtetraspora rubra* ATCC 27031;
MTSALMO = *Microtetraspora salmonea* ATCC 33580;
NOAFR1 = *Nocardiopsis africana* DSM 43748;
SACCAER = *Saccharothrix aerocolonigenes* NRRL B-3298;
SPAMETH = *Streptosporangium amethystogenes* DSM 43179;
SPVIRIDO = *Streptosporangium viridogriseum* ATCC 25242;
STALBUS = *Streptomyces albus* DSM 40313

Fermentation

Strain CLCO-002, when cultured under controlled conditions in a suitable medium produces the compounds IB-97224 and IB-97225. This strain is grown in an aqueous nutrient medium, under aerobic and mesophilic conditions, preferably between 22° C. and 35° C. at a pH ranging between 6.0 and 8.0. A wide variety of liquid culture media can be utilised for the cultivation of the organism, useful media are those that include an assimilable carbon source, such as starch, dextrin, sugar molasses, glycerol, glucose and the like, an assimilable nitrogen source such as proteins, protein hydrolysates, defatted meals, corn steep, and the like, and useful inorganic anions and cations such as sodium, magnesium, potassium, ammonium, sulphate, chloride, phosphate, carbonate, and the like. Trace elements may be added also. Aeration is preferably achieved by supplying air to the fermentation medium. Agitation is provided by a mechanical impeller. Conventional fermentation tanks have been found to be well suited for carrying out the cultivation of this organism. The addition of nutrients and pH control as well as antifoaming agents during the various stages of fermentation may be needed for increasing production and avoid foaming.

The required steps needed for production of these compounds by the preferred organism are:

Start with frozen or lyophilised mycelium. Obtain mycelial mass culturing the initial cells in shake flasks with a culture medium containing some of the ingredients described above at mesophilic temperatures and in aerobic conditions, this step may be repeated several times, as needed, and the material collected will be used as an inoculum to seed one or several fermentation tanks with any appropriate culture medium, if desired these tanks can be utilised also as inoculum, and this step can be repeated several times when needed, or they can serve as the production stage, depending on the broth volume needed. The production stage can last from very few days to more than one week, depending on strain, inoculum stages, temperature and other conditions. Once the fermentation has reached its maximum yield can be harvested for the isolation of the new compounds.

Production medium may be different than that used as inoculum. In Table 2 typical media are described that can be used for inoculum and production of these new compounds:

TABLE 2

| Inoculum medium (g/liter) | | Production medium (g/liter) | |
|---|---|---|---|
| Dextrose | 5 | Dextrose | 5 |
| Starch | 20 | Dextrin | 20 |
| Beef extract | 3 | Soybean meal | 3 |
| Yeast extract | 5 | Yeast extract | 5 |
| Peptone | 5 | Peptone | 1 |
| $CaCO_3$ | 4 | $CaCO_3$ | 4 |
| NaCl | 4 | NaCl | 5 |
| $Na_2SO_4$ | 1 | $Na_2SO_4$ | 2.5 |
| KCl | 0.5 | KCl | 0.5 |
| $MgCl_2$ | 2 | $MgCl_2$ | 0.5 |
| $K_2HPO_4$ | 0.5 | $K_2HPO_4$ | 0.5 |
| | | $(NH_4)_2SO_4$ | 0.5 |
| Tap water to 1 000 ml | | | |

Production of these compounds can be monitored by whole broth assay against A-549 or any other sensitive cell or by HPLC or any other method with enough sensitivity.

Isolation of IB-97224 and IB-97225

Alkaloids IB-97224 and IB-97225 can be isolated from the mycelia cake by extraction with a suitable mixture of solvent such as $CHCl_3:CH_3OH:H_2O$. The activity is concentrated in the lower layer. The extracts from two repeated extractions can be combined and evaporated to dryness in vacuo.

Separation and purification of IB-97224 and IB-97225 from the crude active extract can be performed by the use of the proper combination of conventional chromatographic techniques.

Fractionation can be guided by the antitumor activity of fractions, or by TLC visualized with vanillin in conc. $H_2SO_4$, or analytical HPLC with photodiode-array detector. HPLC analysis are performed at room temperature (Waters RCM 8×10, 8C18 10 μm cartridge) using as mobile phase acetonitrile-sodium hydrogenphosphate 0.025M pH=3 (75:25) and a flow rate of 2 ml/min. and plotted at 290 nm. Compounds of interest showed retention times of 3.92 and 3.29 minutes to IB-97224 and IB-97225 respectively.

The spectral data given below enables the compounds to be identified as IB-97224 and IB-97225. The various atoms are numbered using the numbering system indicated below. The following abbreviations are used:

IR spectra: w: weak; m: medium; s: strong; br: broad.

NMR spectra: s: singlet; d: doublet; t: triplet; dd: doublet of doublets.

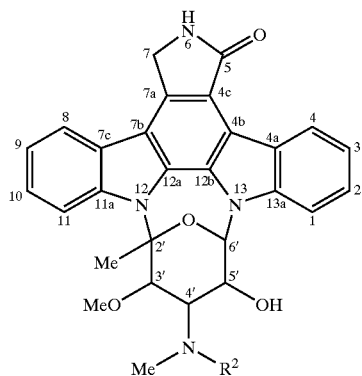

4'-N-methyl-5'-hydroxystaurosporine (IB-97224) ($R^2$=Me)
IR (KBr) $v_{max}$/cm$^{-1}$: 3406 (s, br), 3070 (m), 2925 (s), 2852 (m), 1915 (w, br), 1664 (s), 1583 (s), 1450 (m), 1415 (m), 1391 (s), 1351 (s), 1319 (s), 1281 (s), 1249 (s), 1236 (m), 1223 (m), 1181 (m), 1150 (m), 1117 (s), 1103 (s), 1066 (s), 1018 (m), 988 (m), 887 (w), 835 (w), 816 (w), 742 (s), 698 (w), 664 (w), 636 (w), 609 (w).
$^1$H NMR (300 MHz, CDCl$_3$), δ/ppm: 9.43 (1H, d, J 7.7 Hz, C4H), 7.90 (1H, d, J 7.7 Hz, C8H), 7.76 (1H, d, J 7.7 Hz, C11H), 7.64 (1H, d, J 7.7 Hz, C1H), 7.53 (1H, t, J 7.7 Hz, C2H), 7.45 (1H, t, J 7.7 Hz, C10H), 7.38 (1H, t, J 7.7 Hz, C3H), 7.34 (1H, t, J 7.7 Hz, C9H), 6.52 (1H, s, C6'H), 6.50 (1H, s, N6H), 4.99 (1H, s, C7H), 4.43 (1H, d, J 9.9 Hz, C5'H), 3.95 (1H, s, C3H), 3.02 (1H, d, J 9.9 Hz C4'H), 2.48 (3H, s, CH$_3$), 2.37 (6H, S, N4'(CH$_3$)$_2$), 2.03 (3H, s, CH$_3$O).
$^{13}$C NMR (75 MHz, CDCl$_3$), 173.65 (C5), 137.86 (C11a), 137.12 (C13a), 131.94 (C7a), 130.64 (C12a), 126.79 (C12b), 126.13 (C4), 125.46 (C2), 124.94 (C10), 124.54 (C7c), 123.22 (C4a), 121.49 (C8), 120.43 (C9), 119.98 (C3), 118.89 (C4c), 115.86 (C4b), 114.14 (C7b), 111.46 (C 11), 108.97 (C1), 94.92 (C2'), 91.54 (C6'), 79.30 (C3'), 69.50 (C5'), 66.75 (C4'), 58.36 (CH$_3$O), 45.79 (C7), 41.67 (N4'(CH$_3$)$_2$), 28.00 (CH$_3$).
UV (75:25 CH$_3$CN/0.025 M Na$_2$HPO$_4$ pH 3), $λ_{max}$/nm: 370, 354, 334, 320, 291, 242, 206.
m/z (Fast Atom Bombrdment) 497.2 (MH$^+$).
5'-Hydroxystaurosporine (IB-97225) ($R^2$=H)
IR (KBr) $v_{max}$/cm$^{-1}$: 3415 (s, br), 3070 (m), 2931 (m), 2851 (m), 1991 (w, br), 1664 (s), 1583 (m), 1453 (s), 1416 (m), 1392 (m), 1352 (s), 1317 (s), 1280 (m), 1248 (m), 1236 (m), 1225 (m), 1151 (m), 1130 (m), 1118 (m), 1064 (m), 1036 (m), 1017 (m), 973 (w), 927 (w), 896 (w), 860 (w), 836 (w), 814 (w), 772 (m), 746 (s), 651 (w), 638 (w).
$^1$H NMR (300 MHz, CDCl$_3$), δ/ppm: 9.40 (1H, d, J 7.4 Hz, C4H), 7.89 (1H, d, J 7.4 Hz, C8H), 7.85 (1H, J 7.4, C11H), 7.53 (1H, d, J 8.1 Hz, C1H), 7.44(2H, t, J 7.4 Hz, C2H & C10H), 7.31 (2H, t, J 7.4 Hz, C3H & C9H), 6.49 (1H, d, J 1.2 Hz, C6'H), 6.43 (1H, s, N6H), 4.98 (1H, s, C7H), 4.26 (1H, dd, J 6.8 Hz, 1.2 Hz, C5'H), 4.14 (1H, d, J 2.8 Hz, C3' H), 3.09 (1H, dd, J 6.8 Hz, 2.8 Hz, C4'H), 2.71 (3H, s, CH$_3$O), 2.45 (3H, s, CH$_3$), 2.17 (3H, s, CH$_3$N4').
$^{13}$C NMR (75 MHz, CDCl$_3$), δ/ppm: 173.81 (C5), 138.86 (C11a), 137.05 (C13a), 132.17 (C7a), 130.50 (C12a), 126.89 (C12b), 126.13 (C4), 125.33 (C2), 124.67 (C10), 124.52 (C7c), 123.24 (C4a), 121.01 (C8), 120.32 (C9), 119.92 (C3), 118.56 (C4c), 115.64 (C4b), 114.19 (C7b), 113.50 (C11), 108.10 (C1), 92.37 (C2'), 88.38 (C6'), 80.14 (C3'), 70.03 (C5'), 60.11 (C4'), 59.02 (CH$_3$O), 45.88 (C7), 33.68 (CH$_3$N4'), 28.96 (CH$_3$).
UV (75:25 CH$_3$CN/0.025 M Na$_2$HPO$_4$ pH 3), $λ_{max}$/nm: 370, 354, 334, 320, 291, 242, 206.
m/z (Fast Atom Bombardment) 483.2 (MH$^+$).

Biological Activity

The antitumor activities of IB-97224 and IB-97225 have been determined in vitro in cell cultures of mouse leukemia P-388D$_1$, human lung carcinoma A-549, human colon carcinoma HT-29 and human melanoma SK-MEL-28. The procedure was carried out using the methodology described by Bergeron, et al. (1984), and by Schroeder, et al. (1981).

The present invention will be further illustrated with reference to the following examples which aid in the understanding of the present invention, but which are not to be construed as limitations thereof. All percentages reported herein, unless otherwise specified, are presented by weight. All temperatures are expressed in degrees Celsius. All incubations are carried out at 28° C. and flasks are shaken in an orbital shaker. All media and recipients are sterile and all culture processes aseptic.

EXAMPLE 1

Stock Culture: Whole broth of a pure culture of strain CLCO-002 is preserved frozen in 20% glycerol.

Inoculum: A frozen culture or a well grown slant culture (5% vol.) is used to seed 100 ml of seed medium described previously contained in a 250 cc shake flask. The flask is incubated during 48 hr. 500 ml of the same medium in 2 L Erlenmeyer flask are seeded with 10% of the first stage inoculum. The flask is incubated during 48 h.

Fermentation: With 2.5 L of second stage inoculum seed 50 L of production medium already described in a 75 L fermentation tank. The fermentation is carried out during 96 hours with 400 rpm agitation and airflow of 0.5 V/V.M.

Monitor secondary metabolite production by assay of whole broth against A-549 or by HPLC.

Isolation: 10 L of whole harvested broth was filtrated to separate the biomass and other solids. The mycelial cake was extracted twice with a mixture solvent (2.4 l) of CHCl$_3$:CH$_3$OH:H$_2$O (2:1:1), and the activity was concentrated in the lower layer. The organic solvent was concentrated and evaporated to dryness in vacuo to yield 3.2 g of crude extract. The extract was chromatographed on silica gel "vacuum flash" column. After washing with a mixture of n-hexane-ethyl acetate 1:1, the column was developed with an ethyl acetate-methanol gradient. The progress of the elution was checked for cytotoxicity against A-539 cells and monitored by TLC (chloroform-methanol 9:1) and analytical reverse phase HPLC-photodiode array. Further purification of active fractions (250 mg) was achieved by column chromatography on silica gel and the activity was eluted with chloroform-methanol 92:8 and 95:5. Each of these fractions were chromatographed on a column of C18 reversed phase and eluted with methanol-water 65:35 to give 12 mg of staurosporine, 4 mg of IB-97224, and 8 mg of IB-97225.

Biological activity: The antitumor cells employed have been P-388D$_1$ (suspension culture of a lymphoid neoplasm from DBA/2 mouse), A-549 (monolayer culture of a human macrocytic lung carcinoma), HT-29 (monolayer culture of a human colon carcinoma), and SK-MEL-28 (monolayer culture of a human melanoma). P-388D$_1$ cells were seeded into 16 mm wells at $1 \times 10^4$ cells per well in 1 ml aliquots of MEM 5FCS containing the indicated concentration of drug. A separate set of cultures without drug was seeded as control of growth to ensure that cells remained in exponential phase of growth. All determinations were carried out duplicated. After three days of incubation at 37° C. in 10% $CO_2$ atmosphere with 98% humidity, the IC$_{50}$ was calculated by comparing the growth in wells with drug with the growth in control wells without the drug. A-549, HT-29, and SK-MEL-28 cells were seeded into 16 mm wells at $2 \times 10^4$ cells per well in 1 ml aliquots of MEM 10FCS containing the indicated concentration of drug. A separate set of cultures without drug were seeded as control of growth to ensure that cells remained in exponential phase of growth. All determinations were carried out duplicated. After three days of incubation at 37° C. in 10% $CO_2$ atmosphere with 98% humidity, the well were stained with 0.1% Crystal Violet. The IC$_{50}$ was calculated by comparing the growth in wells with drug with the growth in control wells without the drug.

In Table 3 are presented the activity expressed as IC$_{50}$ ($\mu$M)

TABLE 3

| Cell line | IC$_{50}$ ($\mu$M) | |
|---|---|---|
| | IB-97224 | IB-97225 |
| P388D$_1$ | 0.04 | 0.02 |
| A-549 | 0.002 | 0.002 |
| HT-29 | 0.004 | 0.004 |
| SK-MEL-28 | 0.004 | 0.002 |

CITED REFERENCES

The following references have been cited herein, and they are hereby incorporated herein by reference:
Nishizuka, Y., *Nature* 334: 661–665, 1988
Nishizuka, Y., *Nature* 308: 693–698, 1984
Shirling B. E., and Gotlieb D., *Int. J. Syst. Bacteriol.* 16: 313–340, 1966
American Type Culture Catalog 17 th edition, 1989. Rockville, Md. U.S.A.
Atlas R. M., Handbook of Microbiological Media, 1993 CRC Inc. Boca Raton, Fla. USA
Luedemann G. M. *Personal Communication*
Hasegawa T., Takizawa M., and Tanida S., *J. Gen. Appl. Microbiol.* 29: 319–322, 1983
Van der Auwera P., Labbe M., Mayberry W. R., Ferguson K. P., and Lambe D. W. Jr., *J. Microbiol. Methods* 4: 265–275, 1986
Bergeron et al., *Biochem. Biophys. Res. Comm.,* 121: 848–854, 1984
Schroeder et al., *J. Med. Chem.,* 24: 1078, 1981

What is claimed is:
1. Compounds of formula (1):

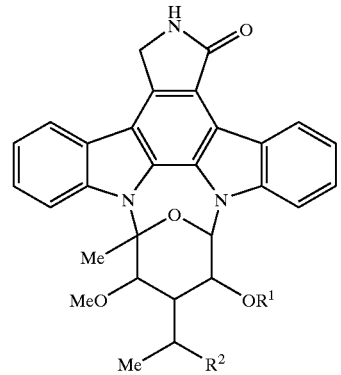

(1)

wherein:
R$^1$ is a hydrogen atom, an alkyl group having 1 to 6 carbon atoms or an alkoxy group having 1 to 6 carbon atoms; and
R$^2$ is a hydrogen atom, an alkyl group having 1 to 6 carbon atoms or an alkoxy group having 1 to 6 carbon atoms;
and pharmaceutically acceptable salts thereof.

2. A compound according to claim 1, wherein R$^1$ is a hydrogen atom or an alkyl group having 1 to 4 carbon atoms.

3. A compound according to claim 2, wherein R$^1$ is a hydrogen atom, a methyl group, or an ethyl group.

4. A compound according to claim 3, wherein R$^1$ is a hydrogen atom.

5. A compound according to claim 1, wherein R$^2$ is a hydrogen atom or an alkyl group having 1 to 4 carbon atoms.

6. A compound according to claim 5, wherein R$^2$ is a hydrogen atom, a methyl group, or an ethyl group.

7. A compound according to claim 6, wherein R$^2$ is a hydrogen atom or a methyl group.

8. A compound according to claim 1, wherein:
R$^1$ is a hydrogen atom or an alkyl group having 1 to 4 carbon atoms, and
R$^2$ is a hydrogen atom or an alkyl group having 1 to 4 carbon atoms.

9. A compound according to claim 8, wherein:
R$^1$ is a hydrogen atom, a methyl group, or an ethyl group; and
R$^2$ is a hydrogen atom, a methyl group, or an ethyl group.

10. A compound according to claim 1, wherein R$^1$ is a hydrogen atom and R$^2$ is a methyl group.

11. A compound according to claim 1, wherein R$^1$ and R$^2$ are both hydrogen atoms.

12. A pharmaceutical composition containing as an active ingredient a compound of formula (1) as defined in claim 1, or a pharmaceutically acceptable salt thereof, in conjunction with a pharmaceutically acceptable carrier or diluent.

13. A method for the treatment of malignant tumors in a mammal, comprising administering to a mammal in need of such treatment an effective amount of a compound of formula (1) as defined in claim 1 or a pharmaceutically acceptable salt thereof, wherein the tumor is selected from the group comprising leukemia, lump carcinoma, colon carcinoma, and melanoma.

14. A process for the production of a compound of formula (1), as defined in claim 1, or a pharmaceutically acceptable salt thereof, comprising cultivating a strain of a microorganism capable of producing a compound of formula (1), recovering the compound of formula (1) from the cultured broth, and, optionally, satisfying the recovered compound, wherein the microorganism is an actinomycete strain CLCO-002 (CECT-3347).

* * * * *